United States Patent [19]
Genova et al.

[11] Patent Number: 5,171,448
[45] Date of Patent: Dec. 15, 1992

[54] PROCESS FOR PURIFYING PARAFFIN SULPHONIC ACIDS

[75] Inventors: Calogero Genova, Vizzolo Predabissi, Italy; Irena Blute, Lidingo, Sweden; Edoardo Platone, Asti, Italy

[73] Assignees: Eniricerche S.p.A., Milan; Enimont Augusta S.p.A., Palermo, both of Italy

[21] Appl. No.: 619,887

[22] Filed: Nov. 28, 1990

[30] Foreign Application Priority Data

Dec. 1, 1989 [IT] Italy .............................. 22568 A/89

[51] Int. Cl.[5] ............................................ B01D 11/04
[52] U.S. Cl. .................................. 210/634; 208/337; 562/124
[58] Field of Search ................ 210/634; 562/124; 208/311, 322, 337, 339, 323

[56] References Cited

U.S. PATENT DOCUMENTS 4,310,473  1/1982  Springmann et al. .............. 210/708
4,436,625  3/1984  Grotta et al. ...................... 210/634

FOREIGN PATENT DOCUMENTS 483716  8/1917  France .

Primary Examiner—Frank Sever
Attorney, Agent, or Firm—Hedman, Gibson Costigan

[57] ABSTRACT

A process for separating and recovering paraffin sulphonic acids from mixtures with water and sulphuric acid is described, consisting of: bringing such a mixture into contact under extraction conditions with a saturated aliphatic or cycloaliphatic liquid hydrocarbon; separating an aqueous liquid phase containing sulphuric acid from an organic liquid phase consisting of the extraction solvent containing the paraffin sulphonic acids; and recovering the paraffin sulphonic acids from said organic liquid phase. The process is particularly applicable to products obtained from processes involving the sulphoxidation of paraffins with sulphur dioxide and oxygen, catalyzed by U.V. radiation.

7 Claims, 7 Drawing Sheets

SASA / CYCLOHEXANE / 67% H2SO4

CRUDE SULPHOXIDATION PRODUCT/CYCLOHEXANE H2SO4

PROCESS FOR PURIFYING PARAFFIN SULPHONIC ACIDS

This invention relates to a process for purifying paraffin sulphonic acids from mixtures with water and sulphuric acid. Paraffin sulphonic acids are products known in the art and are used particularly in the detergent and petroleum sectors. An industrial process for producing paraffin sulphonic acids is based on the sulphoxidation of paraffins with a relatively long carbon atom chain. Specifically, according to this process n-paraffins with between about 12 and 18 carbon atoms are interacted with sulphur dioxide and oxygen under the action of U.V. radiation to produce a crude reaction product which is treated to separate the unaltered reactants and recover the useful reaction product. As reported in the description of European patent application publication No. 273,523, this treatment generally leads to the separation of paraffin sulphonic acids free or substantially free of unaltered paraffins, but in mixture with relatively large quantities of aqueous sulphuric acid. The technical problem of separating the paraffin sulphonic acids from such mixtures therefore exists, and the aforesaid European patent application describes a purification process essentially based on liquid/liquid extraction of the mixtures by chlorinated hydrocarbon solvents and especially dichloromethane. It has however been found that the use of such a solvent does not produce completely satisfactory results, and it is also undesirable from the safety aspect.

The object of the present invention is therefore to overcome the aforesaid drawbacks of the known art. A more specific object of the present invention is to provide a process which enables paraffin sulphonic acids to be effectively purified using a solvent without undesirable toxic characteristics. In accordance therewith the present invention provides a process for separating and recovering paraffin sulphonic acids from mixtures with water and sulphuric acid, characterised by:

bringing such a mixture into contact under extraction conditions with a saturated aliphatic or cycloaliphatic liquid hydrocarbon;

separating an aqueous liquid phase containing sulphuric acid from an organic liquid phase consisting of the extraction solvent containing the paraffin sulphonic acids; and recovering the paraffin sulphonic acids from said organic liquid phase.

The purification treatment of the present invention can be applied to any mixture containing paraffin sulphonic acids, water and sulphuric acid. In particular, the treatment can be conveniently applied to the mixtures resulting from n-paraffin sulphoxidation processes, which contain paraffin sulphonic acids in a quantity of the order of 60-75%, sulphuric acid in a quantity of the order of 6-12% and water in a quantity of the order of 10-20% by weight.

According to the present invention the extraction solvent is chosen from saturated aliphatic or cycloaliphatic hydrocarbons which are liquid under normal conditions. Hexane and cyclohexane are particularly suitable for the purpose. Of the two, cyclohexane is preferred. These solvents, which are free of toxic characteristics, have unexpectedly shown good selectivity in the extraction of paraffin sulphonic acids from their mixtures with sulphuric acid and water.

In the extraction stage the particular weight ratio of extraction solvent to paraffin sulphonic acids can vary generally from 2/1 to 20/1, the chosen ratio depending mainly on the purity required for the paraffin sulphonic acids.

Conveniently in the extraction stage and in the aqueous and organic phase separation stage the operating temperature can range from ambient (about 25° C.) to about 100° C., if necessary applying pressure to maintain the system in the liquid phase. At atmospheric pressure the best results are obtained when operating at a temperature of between 50° and 70° C., this therefore being the preferred temperature range.

In the process of the present invention the concentration of the aqueous sulphuric acid in the mixture subjected to extraction is critical. Specifically, it has been found that if the sulphuric acid concentration exceeds about 80% in the aqueous phase of the starting mixture, acceptable results in terms of purity of the recovered paraffin sulphonic acids are not obtained. The acid concentration is consequently adjusted to 80% by weight or less, and preferably to 55-75% by weight, best results being obtained within this range. The concentration of the aqueous sulphuric acid in the initial mixture can be corrected by simply adding for example water if the acid concentration is too high, or concentrated sulphuric acid if too low.

The paraffin sulphonic acids are finally recovered from the organic liquid phase by conventional methods, for example by evaporating the solvent.

The process of the present invention can be conducted in normal liquid/liquid extraction equipment and aqueous/organic phase separation equipment. The process enables paraffin sulphonic acids, including mixtures thereof, to be purified by a simple and convenient process using non-toxic hydrocarbon solvents. In particular, under suitable temperature and pressure conditions, the use of hexane and cyclohexane enables paraffin sulphonic acids to be obtained having a water and sulphuric acid content of less than 2% by weight.

The following experimental examples are given to better illustrate the present invention.

In these examples the components of the extraction mixture (paraffin sulphonic acids, aqueous sulphuric acid solution and aliphatic hydrocarbon solvent) are brought into mutual contact in suitable weight ratios under extraction conditions. The system then separates into an aqueous phase and an organic phase. The two phases are finally separated and their composition analyzed. In the following experimental examples and in the figures the paraffin sulphonic acid mixtures are indicated by SASA for brevity.

EXAMPLE 1

Synthetic mixtures are prepared by weighing out n-hexane, crude paraffin sulphonic acids and concentrated aqueous sulphuric acid. Specifically, the paraffin sulphonic acids and aqueous sulphuric acid are mixed together in unit weight ratio and the solvent added to obtain mixtures of 50%, 60%, 70%, 80% and 90% by weight. In the particular case involving the use of n-hexane as solvent two aqueous sulphuric acid concentrations, namely 60% and 77% by weight, are used. In the obtained mixtures the effective aqueous sulphuric acid concentration is 58% and 74% by weight respectively, and the weight ratio of SASA to sulphuric acid is 1.45 and 1.13 respectively for the two systems.

The following experimental procedure is followed:
the samples are prepared as described heretofore;
after energetic stirring the samples are left standing until the aqueous phase completely separates from the organic phase;
the n-hexane is distilled off under vacuum; from the organic phase;
the sulphuric acid, SASA and water contents of the aqueous phase and of the residue from the organic phase distillation are analyzed.

Figure 1:
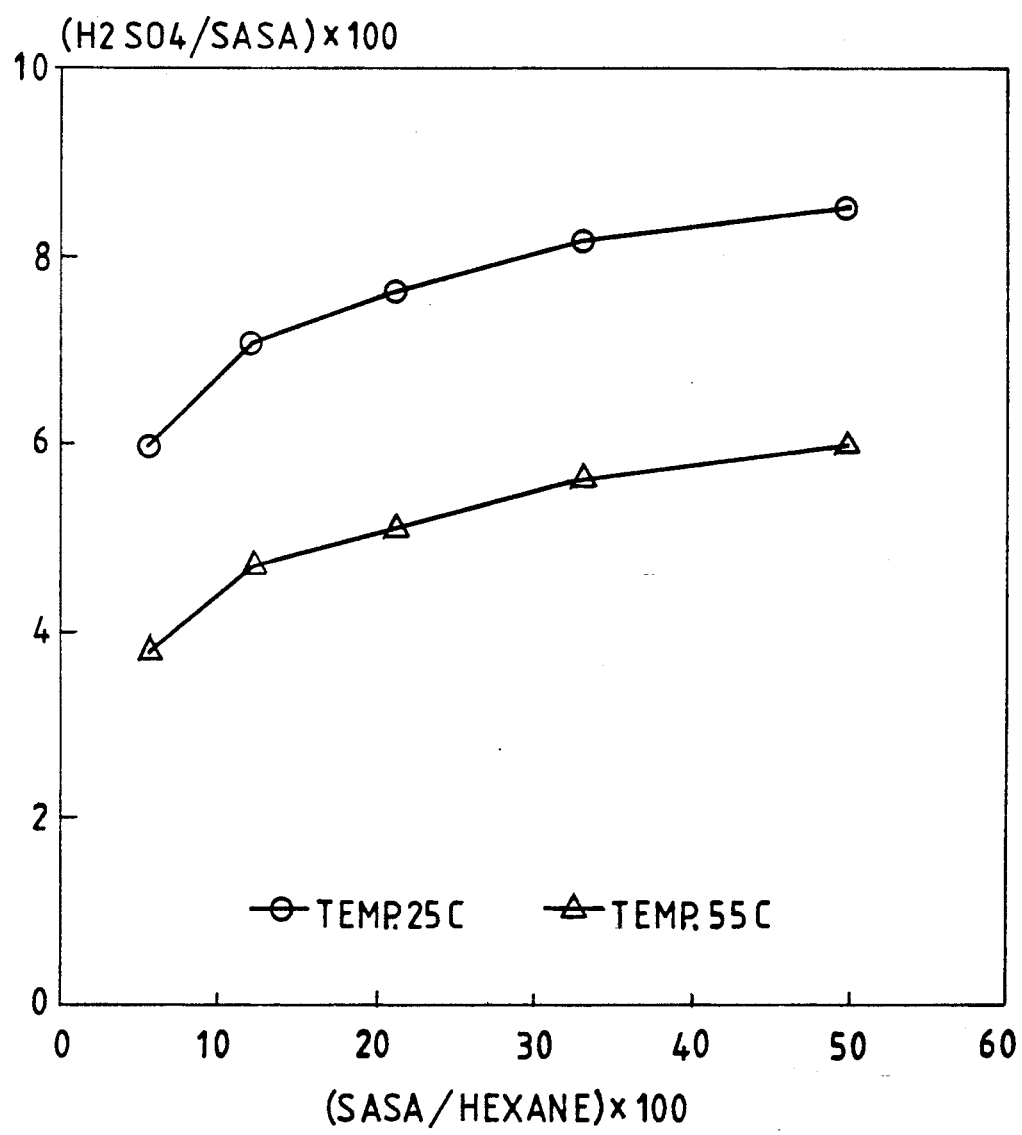
FIG. 1 shows SASA/Hexane (58%$H_2SO_4$)

FIG. 1 shows the degree of purity, expressed as percentage of sulphuric acid in the recovered paraffin sulphonic acid for the n-hexane/58 wt % aqueous sulphuric acid/SASA system, plotted against n-hexane concentration for two different temperatures (25° and 55° C.). The vertical axis represents the weight ratio (expressed as percentage units) of sulphuric acid to paraffin sulphonic acid as the SASA purity parameter, and the horizontal axis represents the weight ratio (in percentage units) of SASA to n-hexane in the initial sample.

Figure 2:
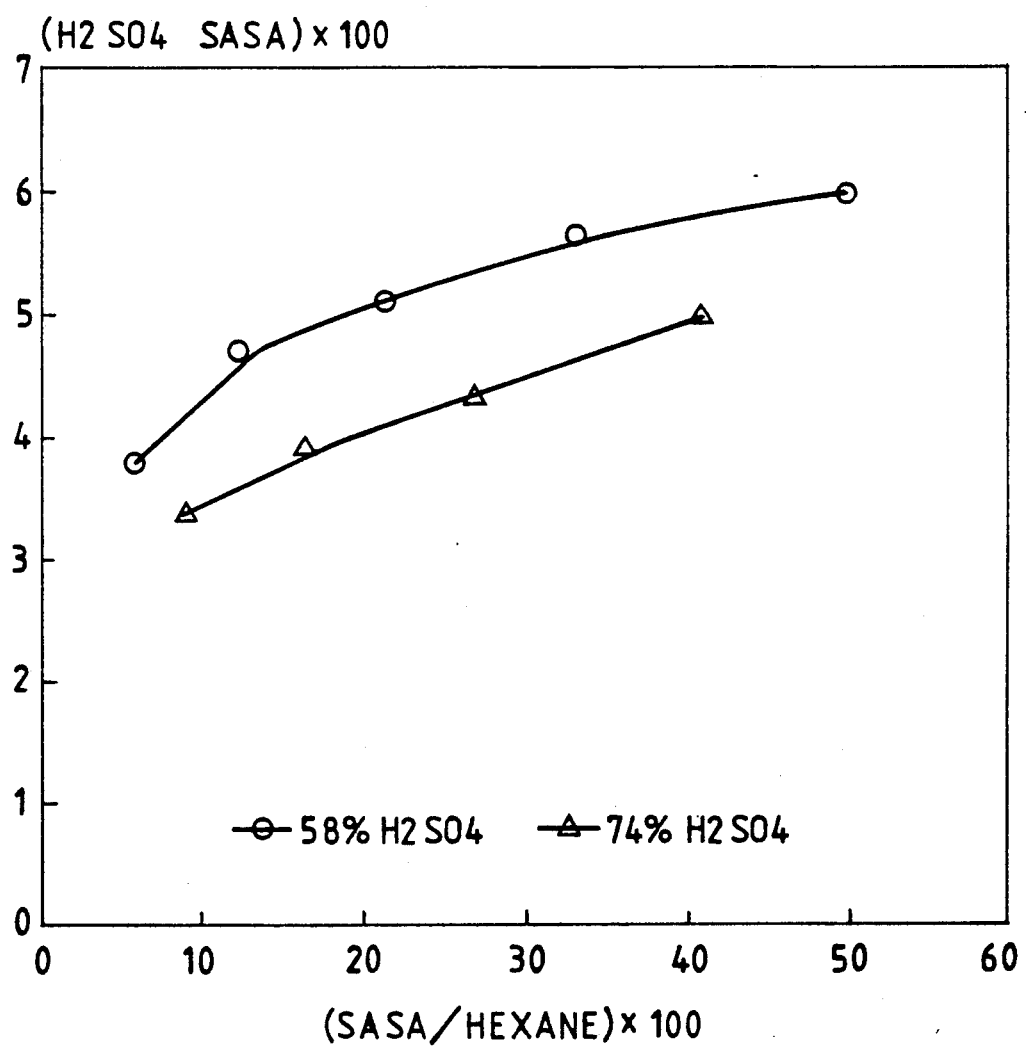
FIG. 2 shows SASA/Hexane/AQ.$H_2SO_4$; T=55C.

FIG. 2 shows the influence of sulphuric acid concentration on SASA purity for the n-hexane/sulphuric acid/paraffin sulphonic acid system at the temperature of 55° C. 60 wt % and 77 wt % sulphuric acid are used respectively.

Both at 25° C. and 55° C. the aqueous phases which separate consist of water and sulphuric acid with possible impurities, but no presence of SASA, independently of the sulphuric acid concentration used.

EXAMPLE 2

Following the procedure described in Example 1, the behaviour of the system using cyclohexane as extraction solvent is analyzed. Aqueous sulphuric acid solutions of 60%, 70%, 80% and 90% by weight are used. In the obtained mixtures the final aqueous sulphuric acid concentration is 58%, 67%, 77% and 86% by weight respectively, the SASA/sulphuric acid weight ratio for the various systems being 1.45, 1.24, 1.09 and 0.97 resectively.

Figure 4:
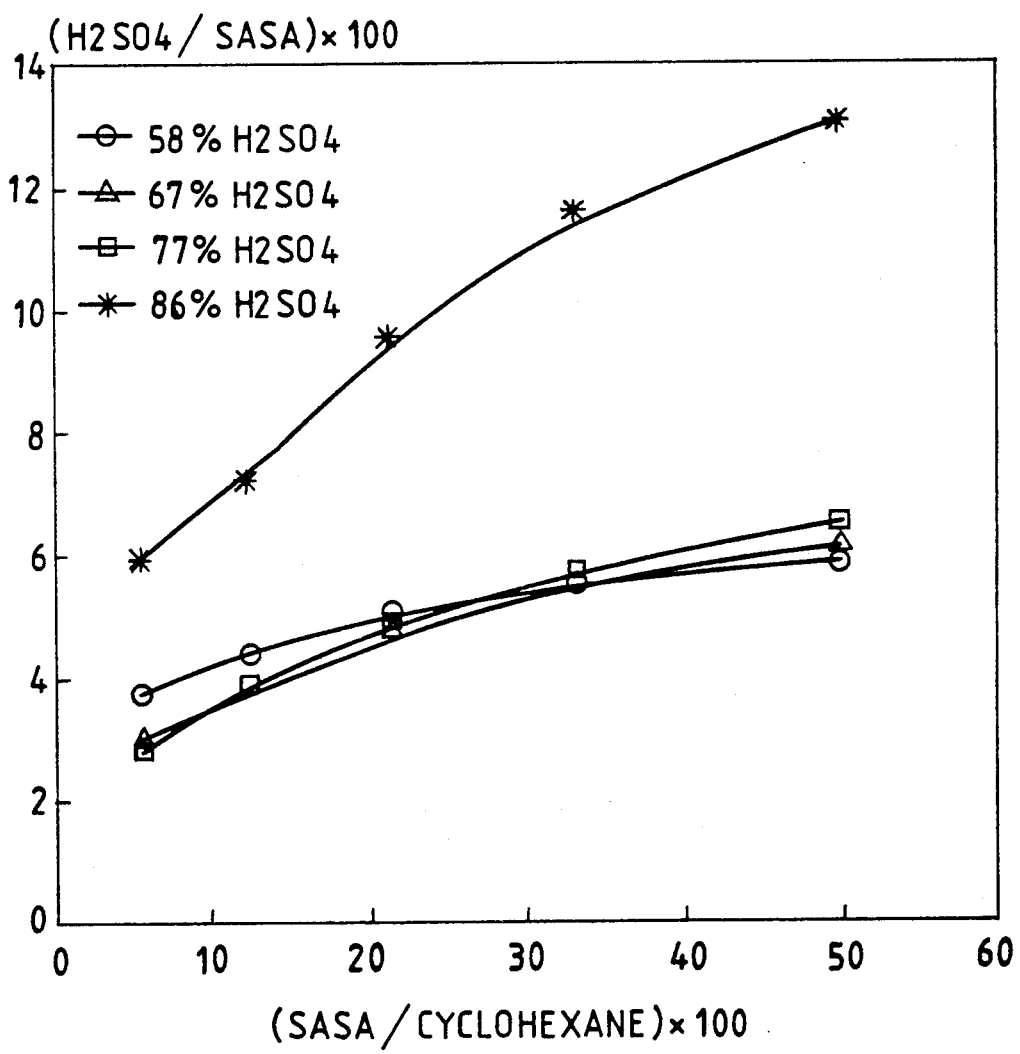
FIG. 4 shows SASA/Cyclohexane/AQ./$H_2SO_4$, T=25C.
Figure 5:
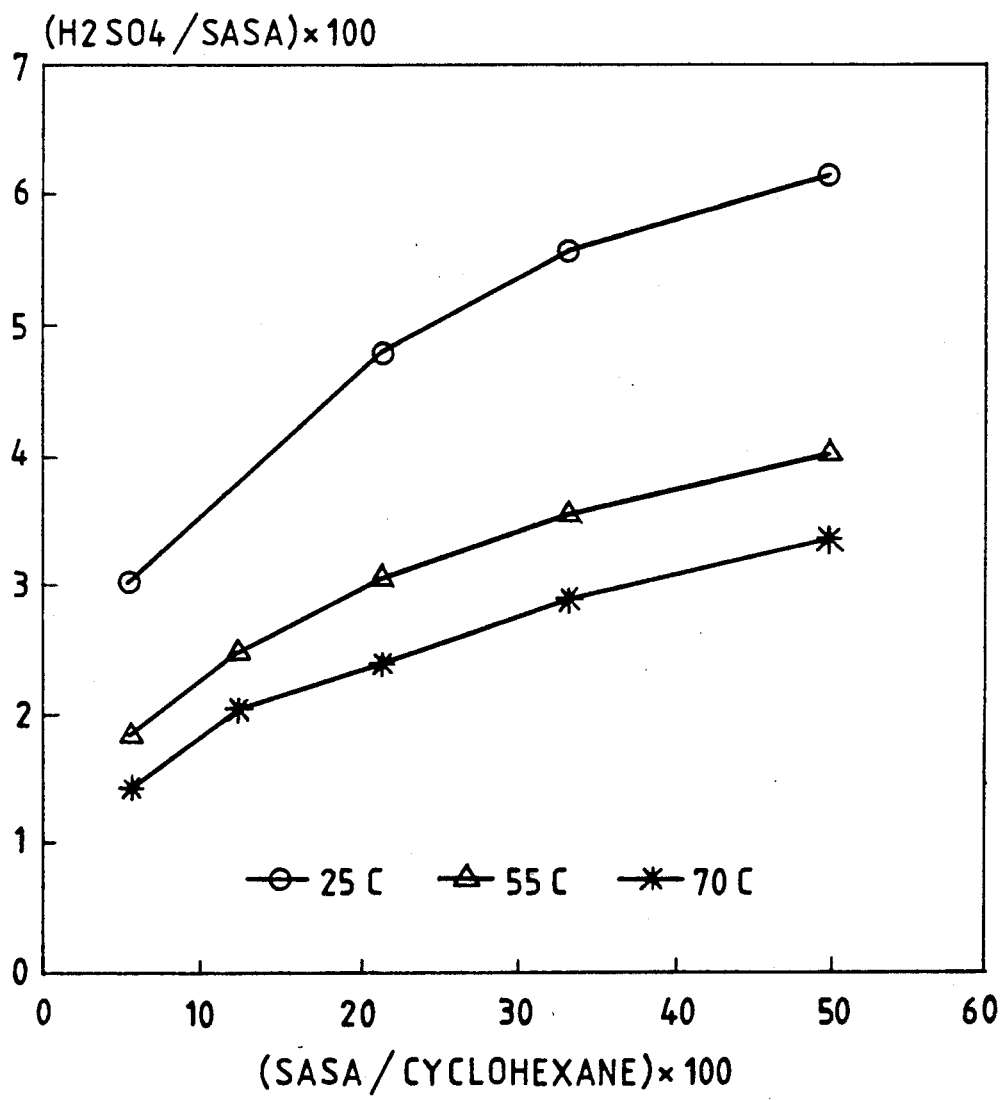
FIG. 5 shows SASA/Cyclohexane/67% $H_2SO_4$.
Figure 6:
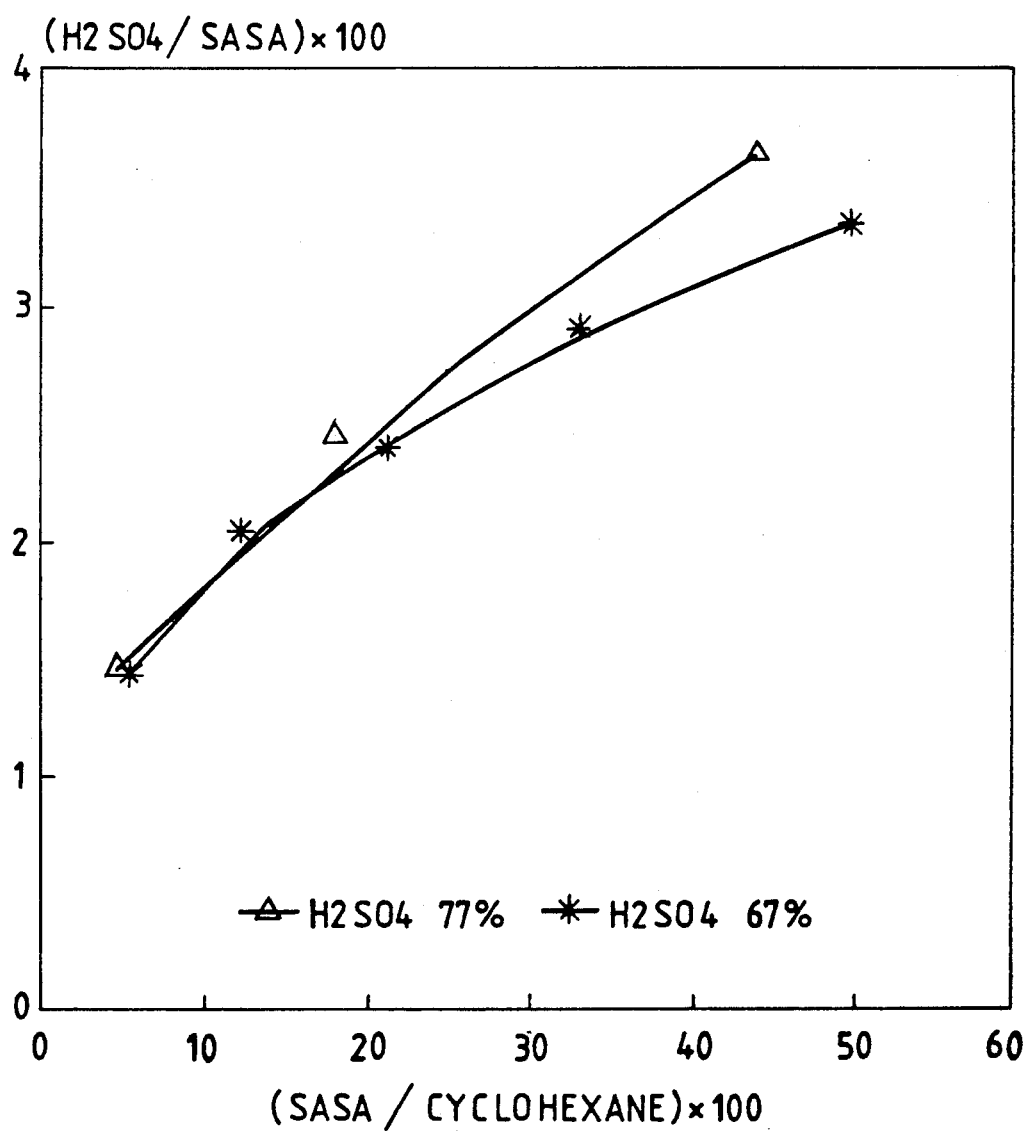
FIG. 6 shows SASA/Cyclohexane/AQ./$H_2SO_4$.

FIG. 4 shows the influence of aqueous sulphuric acid concentration of SASA purity at a temperature of 25° C. using cyclohexane as extraction solvent. FIG. 5 shows the influence of temperature on SASA purity for the cyclohexane/67 wt % sulphuric acid/SASA system. FIG. 6 shows the influence of aqueous sulphuric acid concentration (67 wt % and 77 wt % respectively) on the refined SASA purity, operating at 70° C.

With reference to FIG. 4, it can be seen that within the 55 wt %-75 wt % sulphuric acid concentration range there are no substantial variations and the curves can be practically superimposed, whereas at high sulphuric acid concentrations there is a large increase in the sulphuric acid quantity contained in the recovered SASA. In FIG. 5 it can be seen that the sulphuric acid content of the recovered SASA reduces progressively with increase in system temperature.

EXAMPLE 3

Following the procedure described in Example 1 the system behaviour is analyzed as a function of the extraction solvent (n-hexane and cyclohexane).

Figure 3:
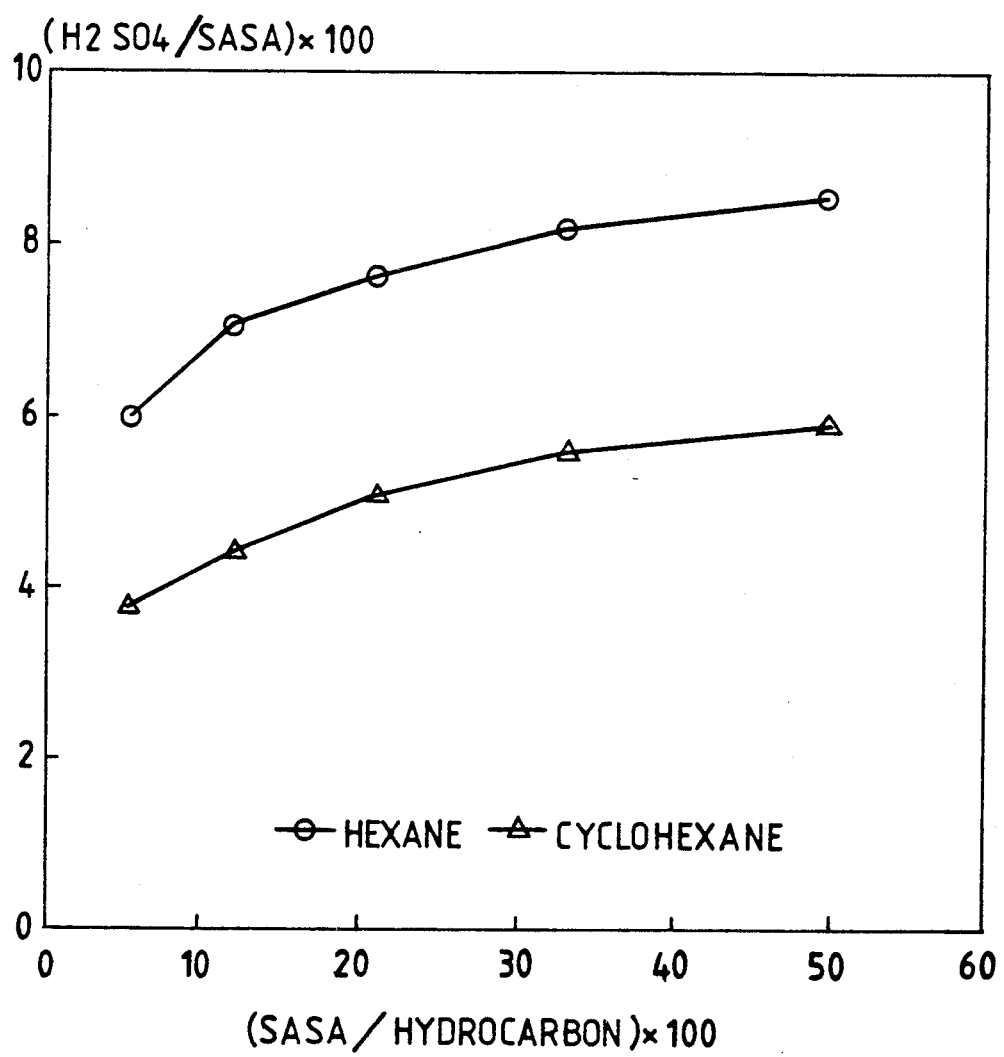
FIG. 3 shows SASA/Hydrocarbon/58%$H_2SO_4$, T=25C.

FIG. 3 compares the degree of purity in terms of weight percentage of sulphuric acid in the purified SASA in tests conducted at 25° C. using 58 wt % aqueous sulphuric acid, with n-hexane and cyclohexane as extraction solvent respectively.

As can be seen from the figure the use of cyclohexane results in an SASA with a lower sulphuric acid content throughout the entire solvent concentration range.

EXAMPLE 4

A crude sulphoxidation product containing 68.4% of SASA (C14–C17 sulphonated paraffins), 8,95% sulphuric acid and 14.4% water by weight is used.

Equal quantities of 80 wt % aqueous sulphuric acid are added to this crude product, the final aqueous sulphuric acid concentration then being 72.16% by weight and the weight ratio of SASA to sulphuric acid being 0.77.

Extraction is then carried out with cyclohexane at 70° C., operating with 70.250 g of the following sample: crude sulphoxidation product 3.511 g, 80 wt % aqueous sulphuric acid 3.509 g, cyclohexane 63.230 g. After separation at 70° C. an organic phase of 66,070 g and an aqueous phase of 4,180 g are obtained. The aqueous phase has the following composition: sulphuric acid 73.67% by weight, water 26% by weight. After solvent evaporation, the organic phase provides a refined SASA mixture (2.814 g) of the following composition: SASA 94.56%, sulphuric acid 1.45%, water 3.99% by weight.

EXAMPLE 5

The procedure of Example 4 is followed using 33.388 g of a system comprising 5.020 g of crude sulphoxidation product, 4.998 g of 80 wt % sulphuric acid and 23.370 g of cyclohexane.

In the initial mixture the aqueous sulphuric acid concentration is 72.08% by weight and the weight ratio of SASA to sulphuric acid is 0.77.

After extraction with cyclohexane 5.950 g of aqueous solution and 27.120 g of organic solution are obtained. The aqueous solution has the following composition: 74.0% sulphuric acid and 24.4% water by weight. After solvent evaporation, the organic phase provides 3.834 g of refined SASA of the following composition: paraffin sulphonic acids 91.97%, sulphuric acid 1.89%, water 6.14% by weight.

EXAMPLE 6

The procedure of Example 4 is followed using 31.982 g of a system comprising 7.989 g of crude sulphoxidation product, 8.001 g of 80 wt % sulphuric acid and 15.992 g of cyclohexane.

In this mixture the aqueous sulphuric acid concentration is 72.2% by weight and the weight ratio of SASA to sulphuric acid is 0.77. After phase separation 9.605 g of an aqueous phase and 22,182 g of an organic phase are obtained. The aqueous phase composition is 73% sulphuric acid and 26.6% water by weight. After solvent evaporation, the organic phase provides 6.220 g of refined SASA of the following composition: 95.23% SASA, 2.66% sulphuric acid, 2.11% water by weight.

EXAMPLE 7

The procedure of Example 4 is followed using 38.591 g of a system comprising 11,258 g of crude sulphoxidation product, 11.290 g of 80 wt % sulphuric acid and 16.047 g of cyclohexane.

In this mixture the aqueous sulphuric acid concentration is 72.13% by weight and the weight ratio of SASA to sulphuric acid is 0.77. After extraction with cyclohexane at 70° C. 13.779 g of aqueous solution and 24.750 g of organic solution are obtained. The aqueous solution has the following composition: 73.4% sulphuric acid and 26.5% water by weight. After solvent evaporation, the organic phase provides 8.669 g of refined SASA of the following composition: 93.61% SASA, 3.01% sulphuric acid, 3.38% water by weight.

Figure 7:
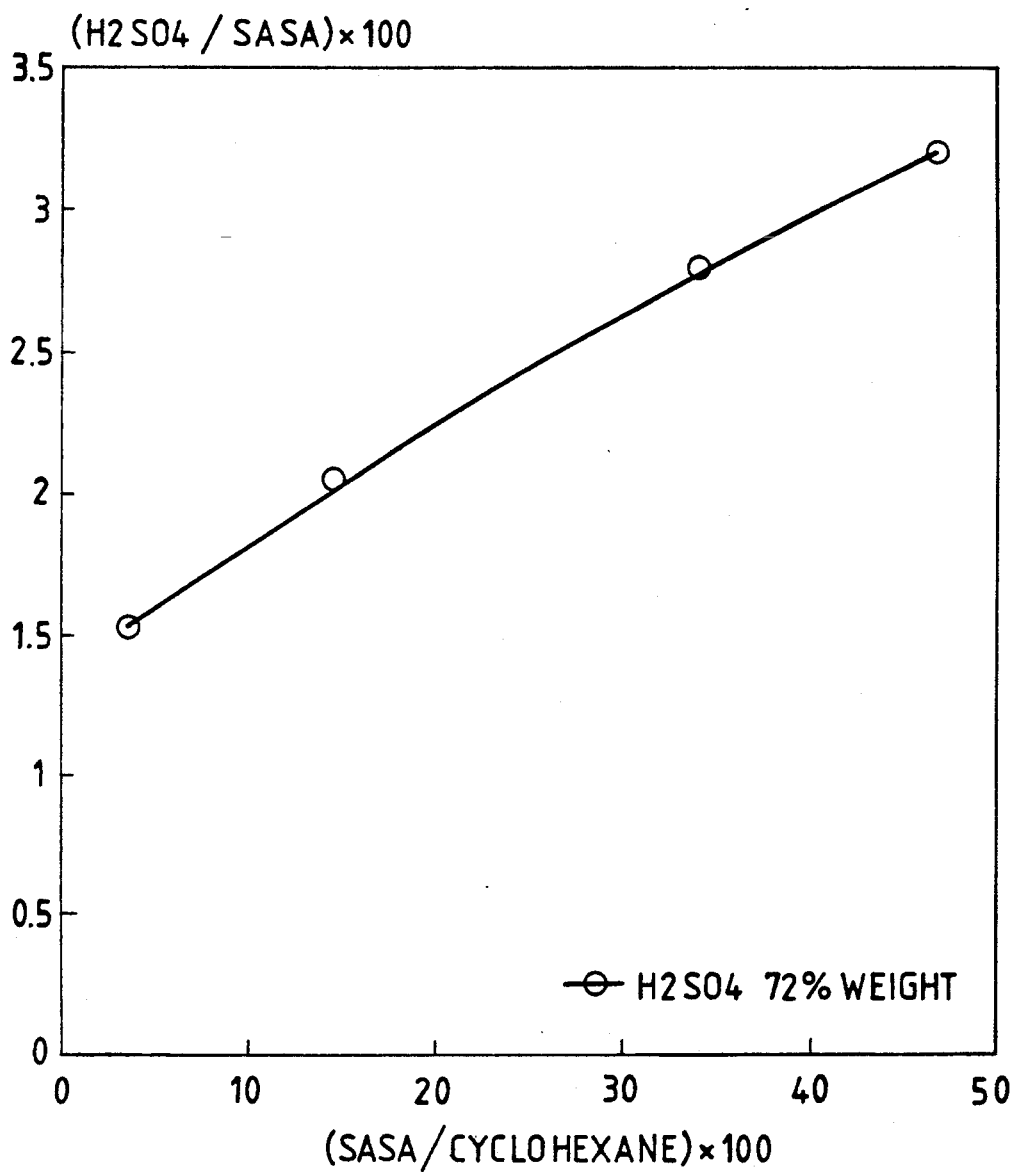
FIG. 7 shows crude Sulphoxidation Product/Cyclohexane/$H_2SO_4$.

The data of Examples 4 to 7 are shown schematically on the graph of FIG. 7.

We claim:

1. A process for separating and recovering paraffin sulphonic acids from mixtures with water and sulfuric acid, comprising:

contacting a mixture derived from a paraffin acid production process involving n-paraffin sulphoxidation and comprising from 60 to 75% by weight of $C_{12}$–$C_{18}$ paraffin sulphonic acids, from 6 to 12% by weight of sulfuric acid and from 10 to 20% by weight of water with a saturated aliphatic liquid hydrocarbon extraction solvent selected from the group consisting of n-hexane to form an aqueous phase and an organic liquid phase; wherein the weight ratio of said extraction solvent to paraffin sulphonic acids is between 2/1 and 20/1;

separating the aqueous phase containing sulfuric acid from the organic liquid phase containing the paraffin sulphonic acids;

recovering the paraffin sulphonic acids from said organic liquid phase.

2. A process as claimed in claim 1, wherein in the extraction stage and in the aqueous and organic phase separation stage the operating temperature is between 25° and 100° C.

3. A process as claimed in claim 2 wherein said operating temperature is between 50° and 70° C.

4. A process as claimed in claim 1, wherein the aqueous sulfuric acid concentration in the extraction mixture is adjusted to 80% by weight or less.

5. A process as claimed in claim 4 wherein said aqueous sulfuric acid concentration is from 55 to 75% by weight.

6. A process as claimed in claim 1 wherein said liquid hydrocarbon comprises cyclohexane.

7. A process for separating and recovering paraffin sulphonic acids from mixtures with water and sulfuric acid, comprising:

contacting a mixture derived from a paraffin acid production process involving n-paraffin sulphoxidation and comprising from 60 to 75% by weight of $C_{12}$–$C_{18}$ paraffin sulphonic acids, from 6 to 12% by weight of sulfuric acid and from 10 to 20% by weight of water with an extraction solvent consisting essentially of n-hexane to form an aqueous phase and an organic liquid phase; wherein the weight ratio of extraction solvent to paraffin sulphonic acids is between 2/1 and 20/1;

separating the aqueous phase containing sulfuric acid from the organic liquid phase containing the paraffin sulphonic acids;

recovering the paraffin sulphonic acids from said organic liquid phase.

* * * * *